(12) United States Patent
Barry et al.

(10) Patent No.: US 12,653,379 B2
(45) Date of Patent: \*Jun. 16, 2026

(54) ENDOSCOPIC SYSTEM WITH ATTACHED INSTRUMENTS

(71) Applicant: American Endoscopic Innovations, LLC, Charlton, MA (US)

(72) Inventors: James P. Barry, Charlton, MA (US); Israel Franco, Chappaqua, NY (US); Michael Grasso, III, Rye, NY (US); Alfio Carroccio, Manhasset, NY (US)

(73) Assignee: American Endoscopic Innovations, LLC, Charlton, MA (US)

( \* ) Notice: Subject to any disclaimer, the term of this patent is extended or adjusted under 35 U.S.C. 154(b) by 250 days.

This patent is subject to a terminal disclaimer.

(21) Appl. No.: 18/518,173

(22) Filed: Nov. 22, 2023

(65) Prior Publication Data

US 2024/0237881 A1 Jul. 18, 2024

Related U.S. Application Data

(63) Continuation of application No. 17/071,362, filed on Oct. 15, 2020, now Pat. No. 12,022,996.

(51) Int. Cl.
| | |
|---|---|
| *A61B 1/00* | (2006.01) |
| *A61B 1/005* | (2006.01) |
| *A61B 1/07* | (2006.01) |

(52) U.S. Cl.
CPC ...... *A61B 1/00087* (2013.01); *A61B 1/00009* (2013.01); *A61B 1/00066* (2013.01); *A61B 1/00098* (2013.01); *A61B 1/00119* (2013.01); *A61B 1/0058* (2013.01); *A61B 1/07* (2013.01)

(58) Field of Classification Search
CPC ........... A61B 1/00087; A61B 1/00009; A61B 1/00066; A61B 1/00098; A61B 1/00119; A61B 17/3478; A61B 1/018; A61M 2025/0092
See application file for complete search history.

(56) References Cited

U.S. PATENT DOCUMENTS

| | | | |
|---|---|---|---|
| 3,297,022 | A | 1/1967 | Wallace |
| 3,941,121 | A | 3/1976 | Olinger et al. |
| 4,211,229 | A | 7/1980 | Wurster |
| 4,249,541 | A | 2/1981 | Pratt |
| 4,759,348 | A | 7/1988 | Cawood |

(Continued)

FOREIGN PATENT DOCUMENTS

| | | |
|---|---|---|
| JP | 5581692 | 9/2014 |

*Primary Examiner* — Anh Tuan T Nguyen
*Assistant Examiner* — Shankar Raj Ghimire
(74) *Attorney, Agent, or Firm* — Fish & Richardson P.C.

(57) ABSTRACT

An endoscopic system having a shaft, a sheath disposed at least partially inside the shaft having a distal end with a leading surface and an inner surface, the leading surface at the distal end of the sheath having rounded edges so as to be atraumatic, an instrument at least partially inside the sheath and movable relative to the sheath along a longitudinal direction of the sheath, the inner surface being sloped so as to deflect the instrument at a predetermined angle as it is moved into contact with the inner surface and out of the sheath, and the sheath being rotatable relative to the shaft so as to change the direction at which the instrument extends from the sheath.

19 Claims, 15 Drawing Sheets

(56)                References Cited

U.S. PATENT DOCUMENTS

| | | | |
|---|---|---|---|
| 5,112,330 | A | 5/1992 | Nishigaki et al. |
| 5,385,561 | A * | 1/1995 | Cerny ................ A61B 17/3417 |
| | | | 604/164.01 |
| 5,928,137 | A * | 7/1999 | Green .................... A61B 90/36 |
| | | | 600/106 |
| 6,071,230 | A | 6/2000 | Henalla |
| 6,083,202 | A | 7/2000 | Smith |
| 6,217,527 | B1 | 4/2001 | Selmon et al. |
| 6,221,049 | B1 | 4/2001 | Selmon et al. |
| 6,425,854 | B1 | 7/2002 | Galt et al. |
| 6,478,775 | B1 | 11/2002 | Galt et al. |
| 6,514,217 | B1 | 2/2003 | Selmon et al. |
| 6,706,017 | B1 * | 3/2004 | Dulguerov .......... A61M 16/085 |
| | | | 128/207.29 |
| 6,719,725 | B2 | 4/2004 | Milo et al. |
| 6,905,489 | B2 * | 6/2005 | Mantell ............. A61B 17/3496 |
| | | | 600/3 |
| 7,004,173 | B2 | 2/2006 | Sparks et al. |
| 7,658,738 | B2 | 2/2010 | Nobis et al. |
| 7,815,565 | B2 | 10/2010 | Stefanchik et al. |
| 2003/0120195 | A1 | 6/2003 | Milo et al. |
| 2004/0176660 | A1 | 9/2004 | Abe |
| 2005/0124852 | A1 | 6/2005 | Bolmsjo et al. |
| 2006/0189940 | A1 | 8/2006 | Kirsch |
| 2010/0056862 | A1 | 3/2010 | Bakos |
| 2013/0324967 | A1 | 12/2013 | Pillai et al. |
| 2014/0005478 | A1 * | 1/2014 | Kennedy, II ....... A61B 1/00066 |
| | | | 600/114 |
| 2014/0236207 | A1 | 8/2014 | Makower et al. |
| 2015/0196193 | A1 * | 7/2015 | Kienzle ............. A61B 1/00114 |
| | | | 600/109 |
| 2016/0174819 | A1 * | 6/2016 | Ouyang ............ A61B 1/00098 |
| | | | 600/105 |
| 2017/0173275 | A1 * | 6/2017 | Anderson ............ A61B 5/0084 |
| 2017/0231474 | A1 | 8/2017 | Saadat et al. |
| 2018/0125516 | A1 | 5/2018 | Chu |
| 2018/0333044 | A1 * | 11/2018 | Jenkins ............. A61B 1/00059 |
| 2020/0069879 | A1 | 3/2020 | Snoke et al. |
| 2021/0177501 | A1 | 6/2021 | Xia et al. |
| 2021/0205012 | A1 | 7/2021 | Hansen et al. |

* cited by examiner

30 DEG TYP

ENDOSCOPIC SYSTEM WITH ATTACHED INSTRUMENTS

CROSS-REFERENCE TO RELATED APPLICATIONS

This application is a continuation application of U.S. application Ser. No. 17/071,362, filed Oct. 15, 2020, which is incorporated by reference.

TECHNICAL FIELD

The present invention relates to endoscopic systems and methods that simplify and reduce the cost of endoscopic surgical procedures and facilitate new minimally invasive procedures. Specifically, the present invention relates to systems and methods for providing a disposable endoscopic instrument that allows for attachment and control of instruments.

BACKGROUND

Currently, a rigid or semi-rigid endoscope is utilized for procedures requiring access to anatomy via a natural, laparoscopic, or percutaneous route. In most cases, a therapeutic or diagnostic procedure is then performed utilizing additional instruments, introduced via the working channel of the endoscope or otherwise. Said instruments, which can include a needle, a cannula, a laser fiber, or others, are typically nonspecific to the endoscope thus providing limited means for control and safety. Therefore, no "system" exists that mates the endoscope to the instruments to form a highly controllable, safer, and simpler procedure for both the user and the patient.

For example, in minimally invasive surgery and procedures, an elongated hollow cannula with sharpened distal end and a proximal fitting to accept a syringe may be passed through the working channel of an endoscope. Alternatively, a flexible laser fiber (typically glass-based, but can be of various compositions) that is attached proximally to a stationary laser can be passed through the working channel of an endoscope and into the human body.

These scenarios present numerous safety issues. Potential damage to the endoscope from the sharp edge of the instrument may occur. Damage may also occur if an incompatible device is passed through an endoscope. Patient safety issues also arise when the needle exits the endoscope without protection. There is also no visual indicator that the device is in "safe" mode with the needle sheathed, and the user must always manually control the needle as there is no fixation to the endoscope. Furthermore, reusable endoscopic devices must be sterilized, and issues exist in reprocessing a narrow cannula.

There are also control issues that arise. For example, control issues arise when the instrument, such as a needle, is sized much smaller than the working channel and is free to move radially therein, or when the needle is unrestrained axially such that protrusion from the endoscope end tip is not fixed. Current devices also only allow the needle to exit axially from the working channel and have no provision to accomplish oblique exit. Additionally, current devices may allow a needle to enter the tissue without restraint and thus perforate too far, causing injury.

In vascular cases, open surgeries or percutaneous procedures are utilized to access the vascular system when intravascular approaches are impractical. Traumatic open surgery is always less preferred than minimally invasive surgery. In addition to the safety and control issues discussed above, access may also be blocked to the target vessel by other anatomy. Limited control of the access device (i.e. needle or other instrument) is problematic due to lack of proximal fixation and axial control. There may also be limited control of the access device due to a fixed exit angle of O degrees. Further, there may be limited ability to cannulate the vessel after access due to instability of the access device.

SUMMARY

The endoscopic systems and devices disclosed herein solve the problems discuss above.

For example, potential damage to the endoscope channel from the sharp edge of an instrument can be solved by placing the instrument in a sheath to guide the instrument in the working channel. In addition, a mechanism providing retraction of the instrument into the sheath and providing an atraumatic tip or bullnose to guide the sheath through the working channel can also prevent endoscope working channel damage during insertion.

Patient safety issues that arise when the instrument exits the endoscope without protection are solved by providing a "safe" and locked position of the actuator in the retracted position. Additionally, a spring mechanism can be provided to assure proper retraction. An optimized optical view of the instrument can be provided by precisely directing the instrument into the field of view via a distal elevator and proximal rotational control. Visual indicia to show the axial position of the instrument and the rotation of the instrument may also be provided to enhance safety.

Adding a coupling to the device at the proximal end that mates with the channel inlet port on the endoscope solves safety issues related to manual control. The coupling may be rotationally adjustable. Safety issues related to sterile reprocessing of a narrow cannula or other instrument are solved by designing the device with inexpensive components such that it may be provided sterile and then disposed of after one use.

Control issues that arise when the instrument diameter is much smaller than the working channel and is free to move radially therein are solved by the addition of the protective sheath that may be precisely sized to fit the working channel (on the outer diameter) and the instrument (on the inner diameter). Control issues that arise when the instrument is unrestrained axially such that protrusion from the endoscope end tip is not fixed is solved by precisely controlling the length of the sheath and providing a mechanism for precise extension and retraction of the instrument.

The addition of an elevator feature at the distal end of the device to direct the instrument off axis solves control issues associated with axial only exits. Control issues such that the instrument may enter the tissue without restraint and thus perforate too far, causing injury is solved by the extent of the oblique exit of the needle being constrained by the proximal control mechanism as well as the natural penetration limited provided by the adjacent atraumatic tip and elevator forming a natural "T" with the instrument and, limiting tissue penetration.

Traumatic open surgery problems are solved by providing an extravascular access approach with a stabilized device having oblique exit, axial, and rotational control. Blocked access to the target vessel by other anatomy is solved by providing an endoscopic view and controlled oblique exit of the needle allowing multiple approach possibilities. Limited control of the access device due to lack of proximal fixation and axial control is solved by fixing the proximal axial control body to the endoscope working channel via a rotationally adjustable coupling. Limited ability to cannulate the vessel after access due to instability of the access device is solved by the proximal fixation and rotational control of the device as well as the oblique exit.

As part of the invention, the device may have one or more new features. For example, the device may have fixation to the endoscope to facilitate single handed control of instrument extension and retraction. The device fixation may be rotationally adjustable and have visual indicia of said rotational position. The instrument, in combination with the atraumatic tip and distal elevator assuring limited penetration into tissue by forming a natural "V" shaped stopping feature.

The device may have a locking mechanism for safe retraction and extension of the instrument. The device may also have a spring-loaded retraction mechanism for safe storage of the instrument. The device may have visual indicia of safe (retracted) and armed (extended) positions. The device may have multiple selectable positions to control distal extension of the instrument. The device may also have multiple distal configurations for tailoring exit direction of the instrument. The instrument may be provided with shape memory of the distal end, and/or the instrument may be pre-bent when required, especially for larger oblique angles of deflection.

The device may also have a shaft length specific to a mating endoscope to assure correct distal protrusion. The device may allow passage of both fluids and mechanical devices. The device may be made of disposable materials, and may be compact, minimizing disposal issues. The device may be a component of a larger system, including a specific endoscope and therapeutic media.

Endoscopic, examination of the anatomy via natural orifice, laparoscopic, endovascular, or percutaneous routes and delivery of therapeutics, energy, and devices to the target anatomy is provided via attachable, disposable instruments. Also, the device discussed herein provides access to a vessel or organ via an endoscopic, laparoscopic, endovascular, or percutaneous route, allowing for cannulation of said vessel or introduction of other therapies.

The endoscopic systems and devices discussed herein can be used to deliver biologics, fluids, barrier materials, surfactants, lubricants, medications, or bulking media into hollow and solid organs under direct endoscopic visualization via an instrument coincident with the working channel of an endoscope. Also, the endoscopic systems and devices can be used to provide access to a vessel or organ via an endoscopic, laparoscopic, endovascular, or percutaneous route, allowing for cannulation of said vessel or introduction of other therapies. Other applications are discussed below.

For example, in Urology, (prostate, bladder, urethra, ureter, and kidney) the systems and devices discussed herein can be used for endoscopic, laparoscopic, endovascular, or percutaneous visualization of the urinary tract and to introduce botulinum toxin and other neuroleptics, chemotherapeutic agents, immunotherapy and immuno-modulators, photodynamic substrates, as well as protective viscous agents and radiotherapy modulators. Additionally, various energy sources may be employed in conjunction with the system.

In GI (Gastro Intestinal), (esophageal, gastric, intestinal, colonic, rectal, and anal pathology), the systems and devices discussed herein can be used for endoscopic, laparoscopic, endovascular, or percutaneous visualization and to introduce sclerosing agents, hemostatic agents, chemotherapeutic agents, immunomodulators, immunotherapy and photodynamic agents.

In ENT (Ear Nose and Throat), the systems and devices discussed herein can be used for endoscopic or percutaneous visualization and to treat trans-nasal and oral lesions and conditions of the larynx, vocal cords, and auditory systems.

In Neurosurgery, the systems and devices discussed herein can be used for endoscopic, laparoscopic, endovascular, or percutaneous visualization of the central and peripheral neurosensory system and to ablate spinal lesions and address intraventricular lesions when placed directly or through an access sheath.

In General Surgery, the systems and devices discussed herein can be used for endoscopic, laparoscopic, endovascular, or percutaneous visualization and to ablate and treat biliary lesions, liver masses, ovarian masses and for treatment of all intra-abdominal organs. The same system and devices described can be also be employed in any duct or tubular structure, such as the biliary system.

In Pulmonary Medicine and Thoracic Surgery, the systems and devices discussed herein can be used for endoscopic, thoracoscopic, endovascular, or percutaneous visualization and treatment of pleural, bronchial, and parenchymal lesions directly or when placed through an access sheath.

In Gynecology, the systems and devices discussed herein can be used for endoscopic, laparoscopic, endovascular, or percutaneous visualization and treatment of lesions involving all gynecologic organs. Specifically, for transvaginal injection of botulinum toxin and other neuroleptics, chemotherapeutic agents, immunotherapy and immuno-modulators, ablative agents, photodynamic substrates, protective viscous agents, and radiotherapy modulators. The therapies may be applied intraluminally, intramuscularly and into fibroids. Additionally, various energy sources may be employed in conjunction with the system.

In addition, for Orthopedics, the systems and devices discussed herein can be used as an adjunctive in arthroscopy to inject harvested cells and materials as well as other biologics into joints and subcartilaginous tissue. The systems and devices may also be used for bone and bone marrow biopsy and harvesting.

In Vascular Surgery, the systems and devices discussed herein can be used for direct visualization as well as endoscopic, laparoscopic, endovascular, or percutaneous visualization of the vascular system. These instruments can be used directly or adjunctively to traverse obstructed vessels, treat endo-leaks and pseudoaneurisms with embolization or ablation, and to treat portal vein obstruction.

The systems and devices discussed herein can also be used In Urology, GI, Vascular, ENT, Neurosurgery, General Surgery, Gynecology, Orthopedic and others to introduce intra-luminal imagers that can be directed onto a lesion thru this device, including intraluminal sonographic probes and confocal imagers for optical coherence tomography, energy sources including laser (e.g. Nd:YAG, 1470 wavelength, Holmium YAG, and Thulium), electrocautery devices including monopolar as well as bipolar energy devices, and ablative energy sources (e.g. high temperature steam, cryotherapy, microwave, High Frequency Ultrasound HIFU)

A variety of tissue sampling devices including biopsy forceps, snares, and extractors can be directed through the systems and devices discussed herein.

In one aspect, an endoscopic system is provided having a shaft, a sheath disposed at least partially inside the shaft having a distal end with a leading surface and an inner surface, the leading surface at the distal end of the sheath having rounded edges so as to be atraumatic, an instrument at least partially inside the sheath and movable relative to the sheath along a longitudinal direction of the sheath, the inner surface being sloped so as to deflect the instrument at a predetermined angle as it is moved into contact with the inner surface and out of the sheath, and the sheath being rotatable relative to the shaft so as to change the direction at which the instrument extends from the sheath.

In another aspect, an endoscopic system is provided having a shaft, an imaging device disposed at a distal end of the shaft, a light source providing light to the distal end of the shaft, a sheath disposed at least partially inside the shaft having a distal end with a leading surface and an inner surface, the leading surface at the distal end of the sheath having rounded edges so as to be atraumatic, an instrument at least partially inside the sheath and movable relative to the sheath along a longitudinal direction of the sheath, the inner surface being sloped so as to deflect the instrument at a predetermined angle as it is moved into contact with the inner surface and out of the sheath, the sheath being rotatable relative to the endoscope so as to change the direction at which the instrument extends from the sheath, a handle disposed at a proximal end of the shaft, the handle having a slidable and locking knob for at least one position of extending the instrument out of the sheath and retracting the instrument into the sheath.

DETAILED DESCRIPTION

Figures 1A, 1B:
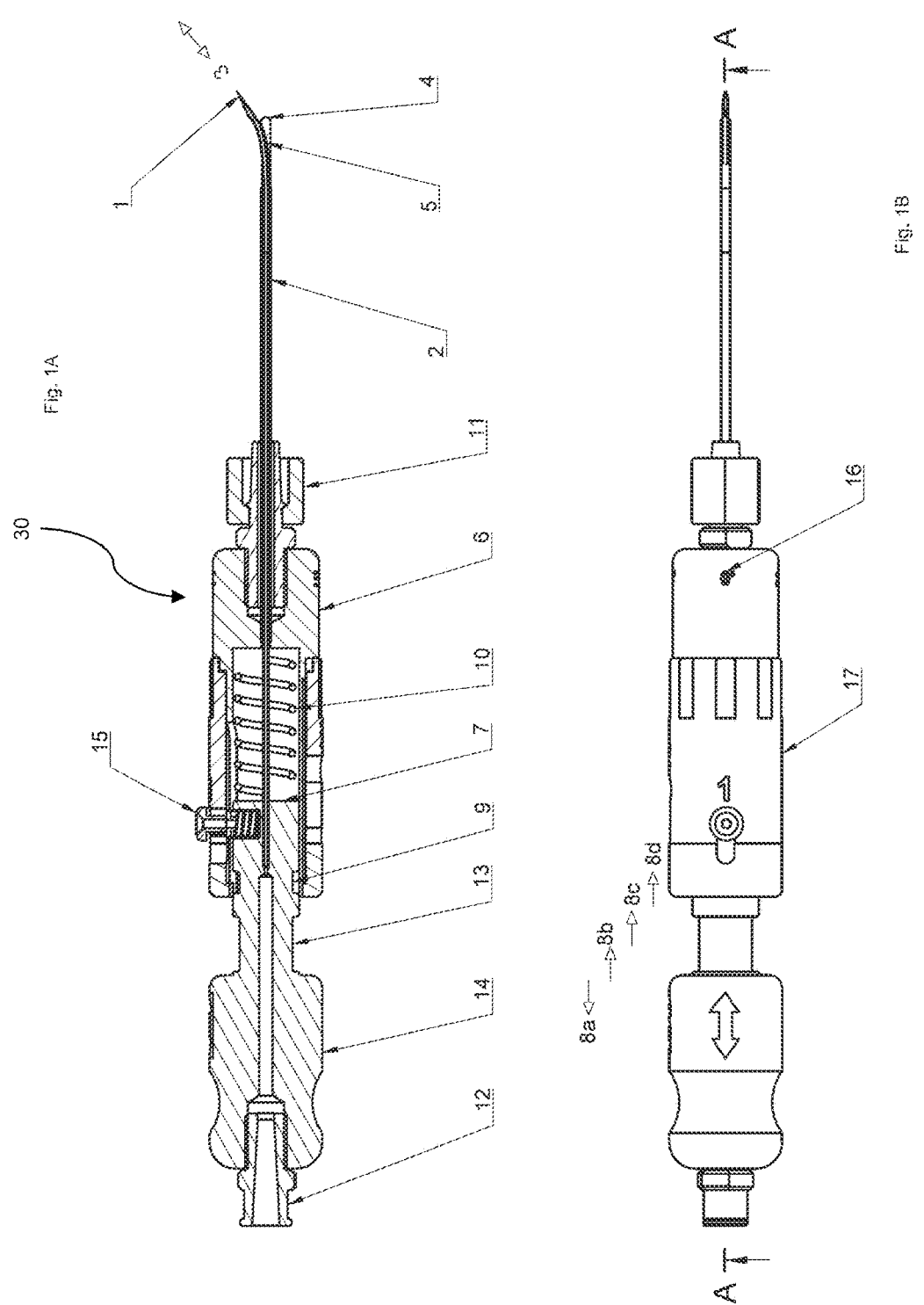
FIG. 1a is a section, side view of the endoscopic system with a needle in an extended position.
FIG. 1b is a top view of the endoscopic system with a needle in an extended position.
Figures 2A, 2B:
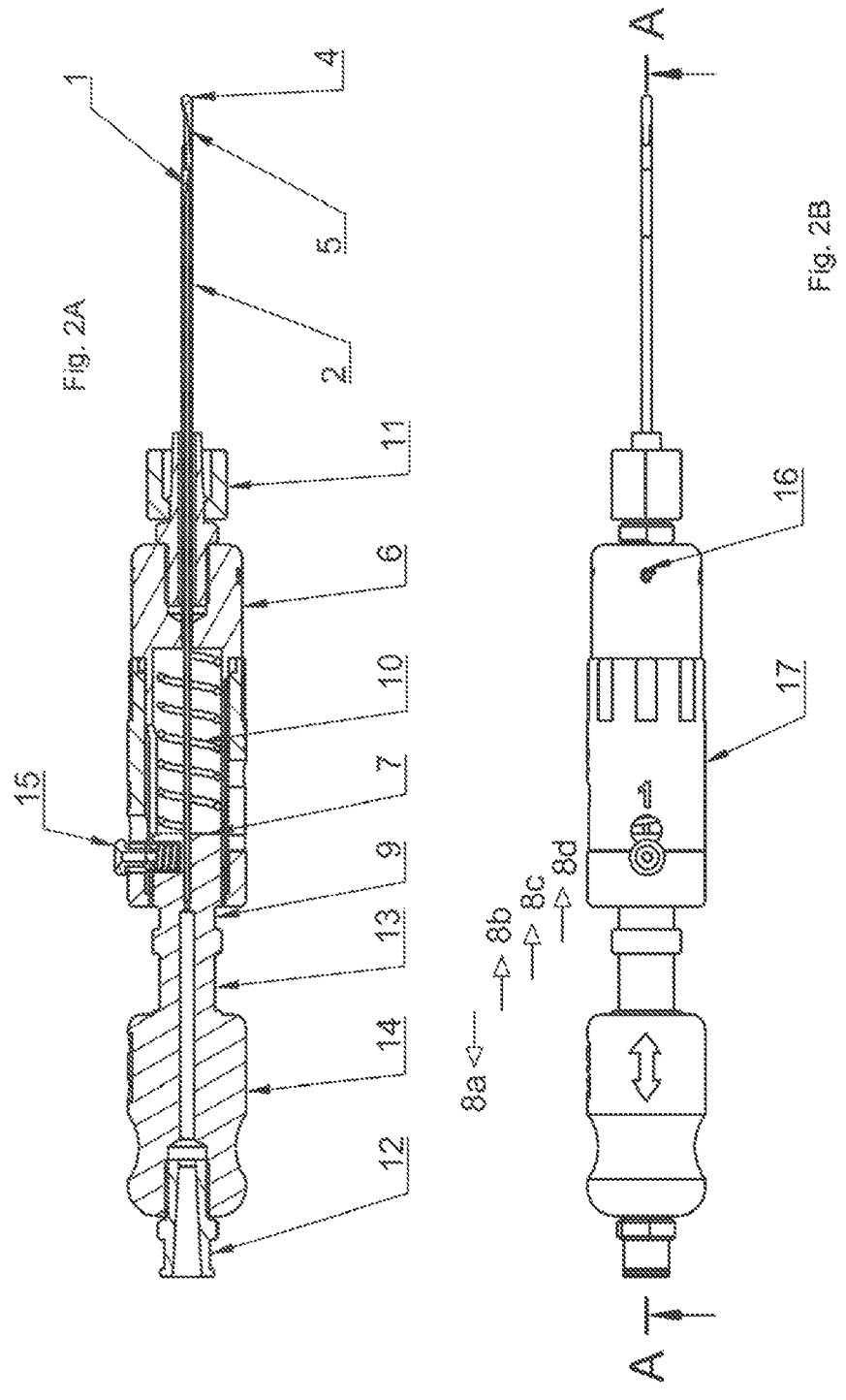
FIG. 2a is a section, side view of the endoscopic system with a needle in a retracted position.
FIG. 2b is a top view of the endoscopic system with a needle in a retracted position.
Figure 3:
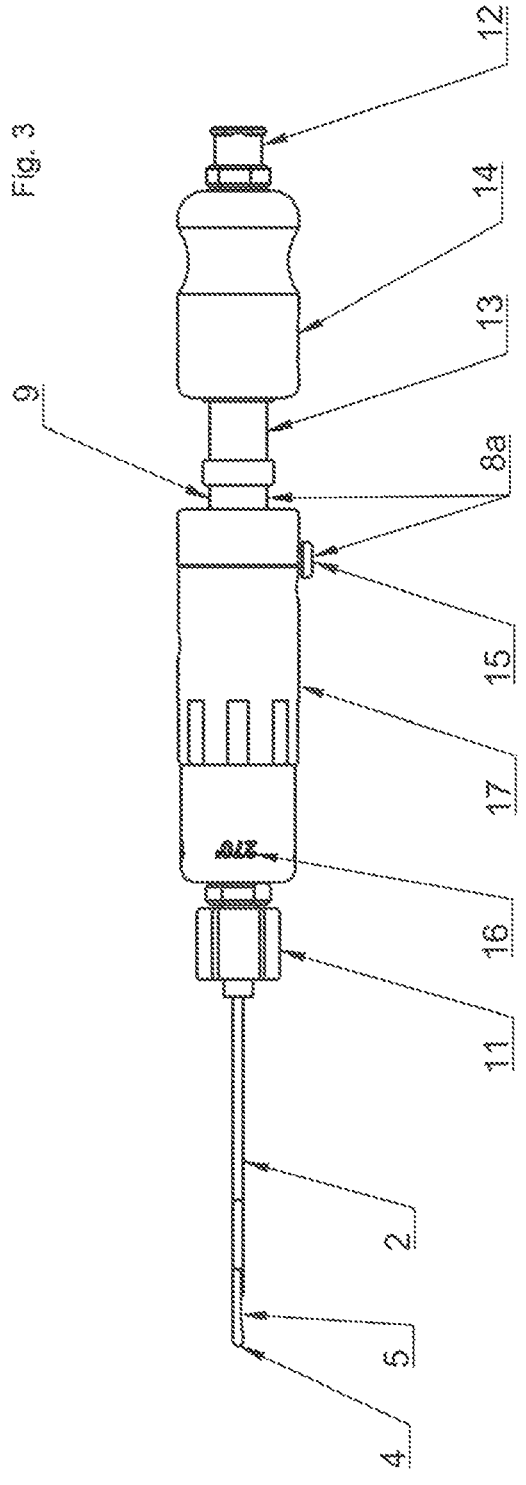
FIG. 3 is a side view of the endoscopic system with a needle in a retracted position.
Figure 4:
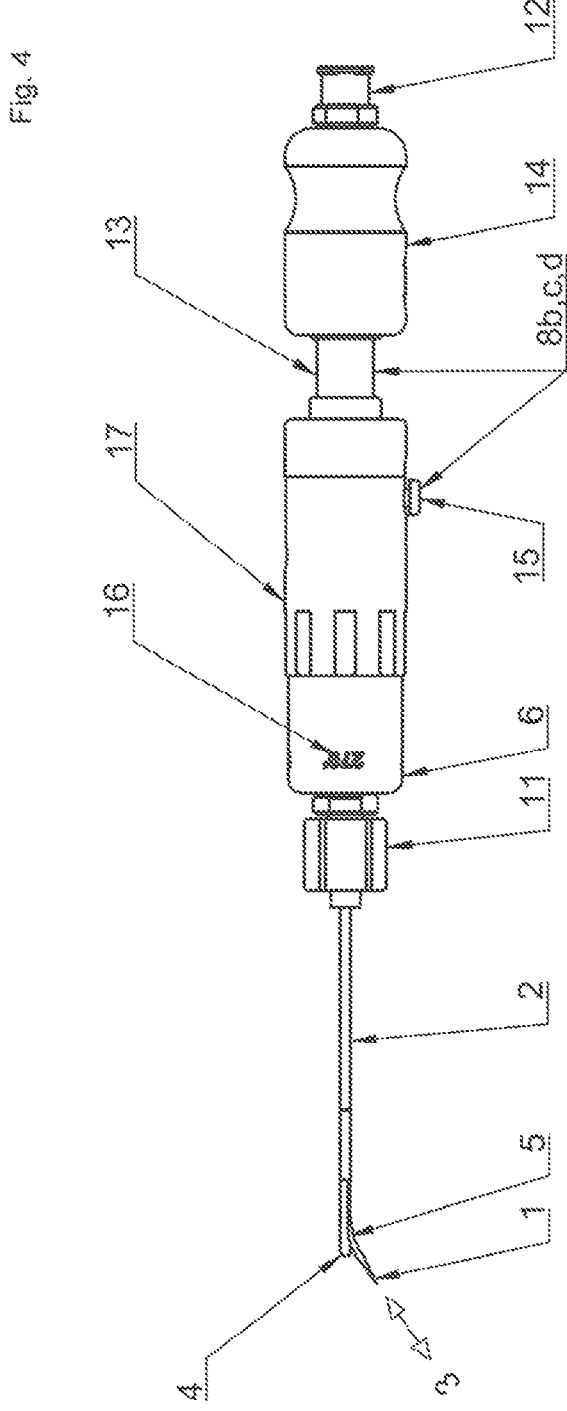
FIG. 4 is a side view of the endoscopic system with a needle in an extended position.
Figures 5A, 5B:
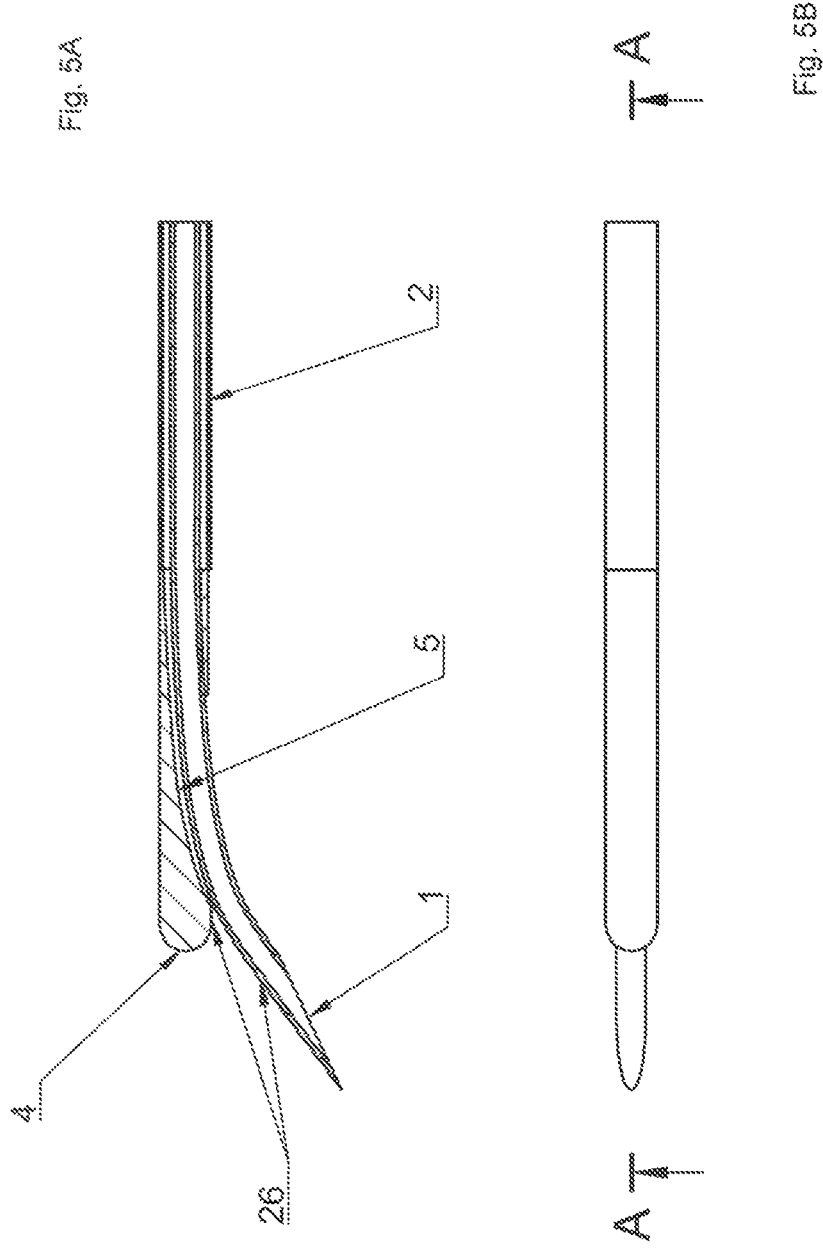
FIG. 5a is a side view of the distal end section of the endoscopic system with a needle in an extended position.
FIG. 5b is a top view of the distal end section of the endoscopic system with a needle in an extended position.
Figure 6:
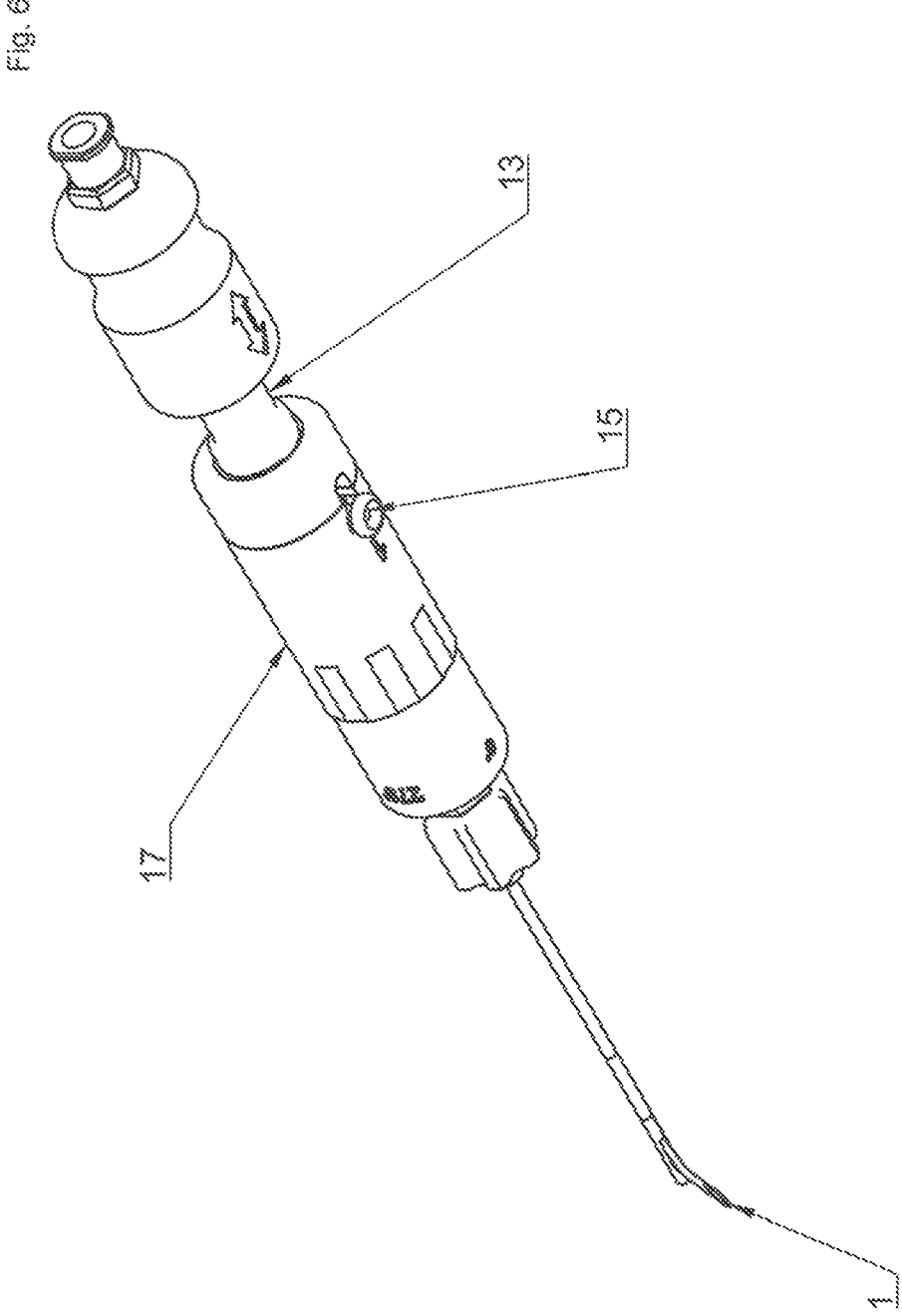
FIG. 6 is an isometric view of the endoscopic system with a needle in an extended position.
Figure 7:
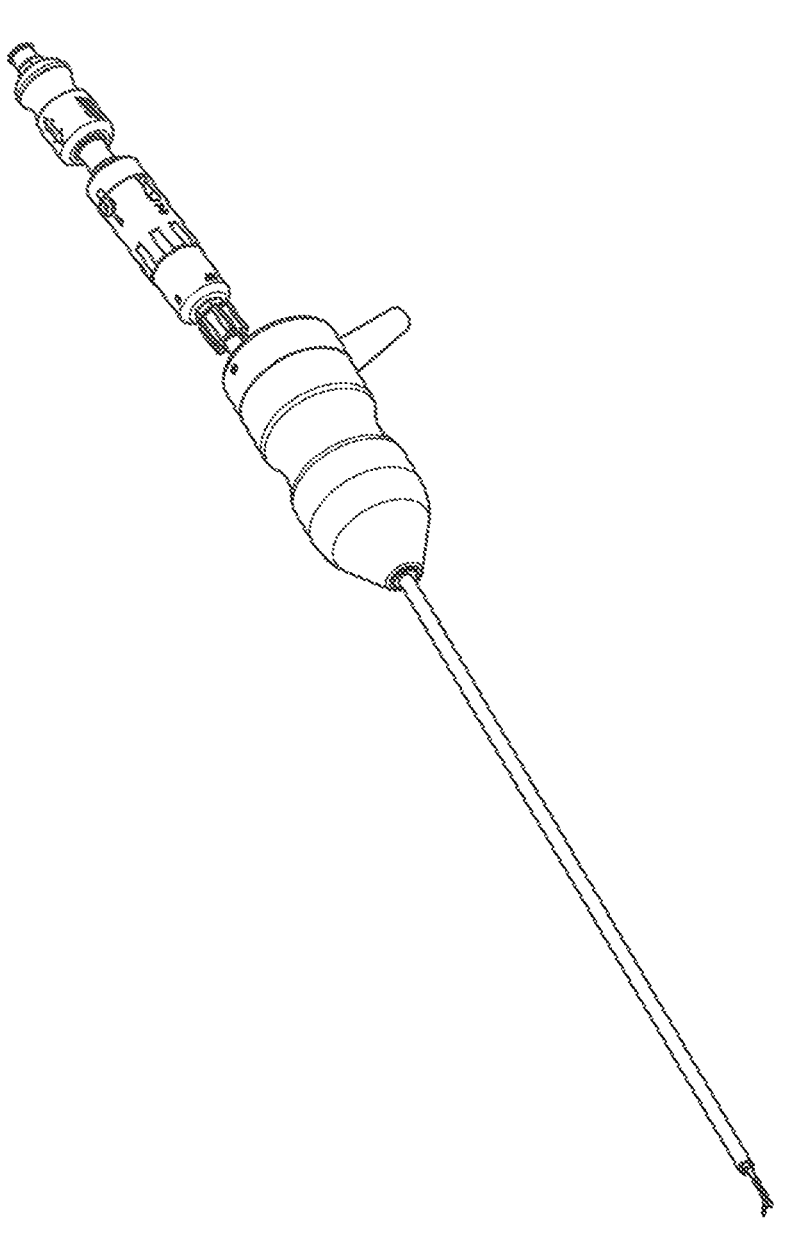
FIG. 7 is an isometric view of the endoscopic system with a needle in an extended position and an attached endoscope.

An endoscopic system is shown in FIGS. 1a-7. The endoscopic system and components used therewith are preferably disposable for hygienic reasons.

An instrument 1, such as a sharpened hollow metal cannula or needle 1, is disposed within a protective sheath 2 of suitable length to pass through an endoscope (such as the one shown in FIG. 7) working channel and exit the distal end of the endoscope. The hollow cannula or needle 1 (hereinafter referred to as a cannula 1 or a needle 1) may be constructed of various metals, including shape memory allows (such as Nitinol) to facilitate curvature when the needle 1 is extended. The needle 1 may be fabricated as pre-bent if desired. The needle 1 and/or sheath 2 may also be plated with a radio-opaque material (such as gold) to enhance visibility when used with X-Ray equipment. The needle 1 and sheath 2 may be of various diameters. The needle 1 may permit passage of both fluids and mechanical devices and instruments. The sheath may be a solid tube or a wound spring of various constructions to facilitate bending and passage through various types of endoscope lumens, including those found in flexible endoscopes. The needle 1 and sheath 2 may be of various lengths to accommodate different endoscopes but should be specifically designed to provide exact protrusion of the device from the distal end of said endoscope.

The needle 1 may also be a different instrument or device, such as a laser fiber or a guide wire.

The needle 1 tip may be cut in any plane, some planes providing advantageous entry to the anatomy and others providing optimum protection to the sharp tip when exiting the cannula. Some planes providing both advantages.

The needle 1 is capable of axial motion along axis 3 within the sheath 2. The needle 1 is designed to specifically interface with a cannulated endoscope. This interface is controlled by the connection type (in this case a rotationally adjustable Luer lock fitting 11 and the precise length of the needle 1 and sheath 2 such that protrusion from the distal end of the endoscope is controlled. A rotationally adjustable ring 17 may be used to control the extension of the needle or hollow cannula 1. When extended, the needle 1, in conjunction with the adjacent atraumatic tip 4, may form a "V" shaped distal configuration 26. In this configuration, the atraumatic tip 4 providing a natural barrier or "stop" to excessive tissue penetration by the needle 1.

The sheath 2 has an atraumatic distal end 4 to prevent patient injury. In addition, the sheath 2 has an elevator or ramp 5 disposed at its distal end, providing an oblique exit out of the sheath 2. The elevator 5 may be configurable to have different exit angles, including any angle between 0 and 90 degrees, inclusive. The elevator 5 may be of various shapes and sizes to direct the needle in the optimal direction.

The needle 1 and sheath 2 are proximally attached to an actuator body 6. The actuator body 6 may be constructed of various materials, metals or plastics and may be produced by injection molding, machining, or additive manufacturing processes. The actuator body 6 includes a proximal knob 14 attached to a slidably locking piston 7 that enables axial motion 3 of the needle 1. The slidably locking piston 7 may have various linear travel limits to provide optimal extension of the needle 1. Additionally, the slidably locking piston 7 may have multiple locking points to provide various extensions of the needle 1 within the same device. For example, the slidably locking piston 7 can be locked in two or more positions (e.g., 8*a*-8*d*) that fix the digital extension of the needle in selectable increments. A visual indicator may be placed on the slidably locking piston 7 to disclose the axial position of the needle 1. For example, a red visual indicator may be placed at location 13 and a green visual indicator can be placed at location 9. Then, as the needle 1 is either in the "safe" or "extended" positions, the appropriate visual indicator will be shown to the operator (compare FIGS. 1*a*, 2*a*). Any known visual indicators, such as letters, symbols, signs, colors, etc. can be used. If the needle 1 is not locked in a position by the slidably locking piston 7, a spring mechanism 10 can return the needle 1 to the "safe" position. A button 15 may also be connected to the spring mechanism to return the need to the "safe" position when pressed.

The actuator body 6 may be connected to the channel fitting (Luer) 11 of an endoscope. This connection being rotationally adjustable. Indicia 16 at the rotationally adjustable connection 11 can show degrees of angular rotation of the distal end, and thus the direction of the needle 1. For example, degree markings may be placed in 90-degree increments or 45-degree increments. Any known visual indicators, such as letters, symbols, signs, colors, etc. can be used.

The needle 1 inner diameter may be connected to an external syringe or fluid delivery system via connection 12, which may be a Luer connection. The Luer connection may be with 'T' style Luer fittings which allow straight through passage of other devices. The connection 12 of the needle 1 inner diameter may also allow for passage of ancillary instruments such as guidewires, etc. to the target organ.

In operation, the device is removed from sterile packaging, checked to assure that it is in "safe" mode with the needle 1 retracted and green indicator ring 9 showing, and inserted into the proximal endoscope working channel. It is then passed through the channel until the Luer Lock fittings 11 meet and are engaged. The device is then connected to the delivery mechanism for the therapeutic media or instruments via a proximal Luer fitting 12. At this point, the device is ready to use.

Due to the length of the device (typically 200 mm or greater) It may be advantageous to "prime" the needle 1. This is accomplished by filling the needle 1 with media and observing the exit of said media via the distal end.

During an endoscopic procedure, the needle 1 extension length is selected by the user via a rotationally adjustable ring 17 located on the actuator body 6. The needle 1 may be extended via a proximal knob 14 attached to piston 7 that employs a "push to lock" linear motion. When in the extended position a red indicator ring 13 will show on the device as a warning. The needle 1 may be retracted by operating a spring-loaded button mechanism 15 placed on the control handle 30 actuator body. This retraction may be assisted by an internal compression spring 10 as a safety device. When in the retracted position a green indicator ring 9 will show on the device as an indicator of "safe" mode. Multiple extensions and retractions are possible. The needle should be retracted and confirmed in "safe" mode before withdrawal of the needle or endoscope from the patient.

Depending on the configuration of the distal end of the device, the needle 1 may exit axially (i.e. no "elevator") or at any oblique angle (such as those between 0 and 90 degrees, inclusive) as provided by numerous elevator designs 5. The oblique angle of exit enabling injection of therapeutics into lumen walls off the axis of the endoscope, ideally within the center of the field of view, or in radial patterns about the axis of the endoscope, all having benefits for specific conditions. Additionally, the device may be used extraluminally, under the direct visualization of the parent endoscope to access vessels or organs enabling the introduction of therapeutics and/or devices.

Figures 8A, 8B:
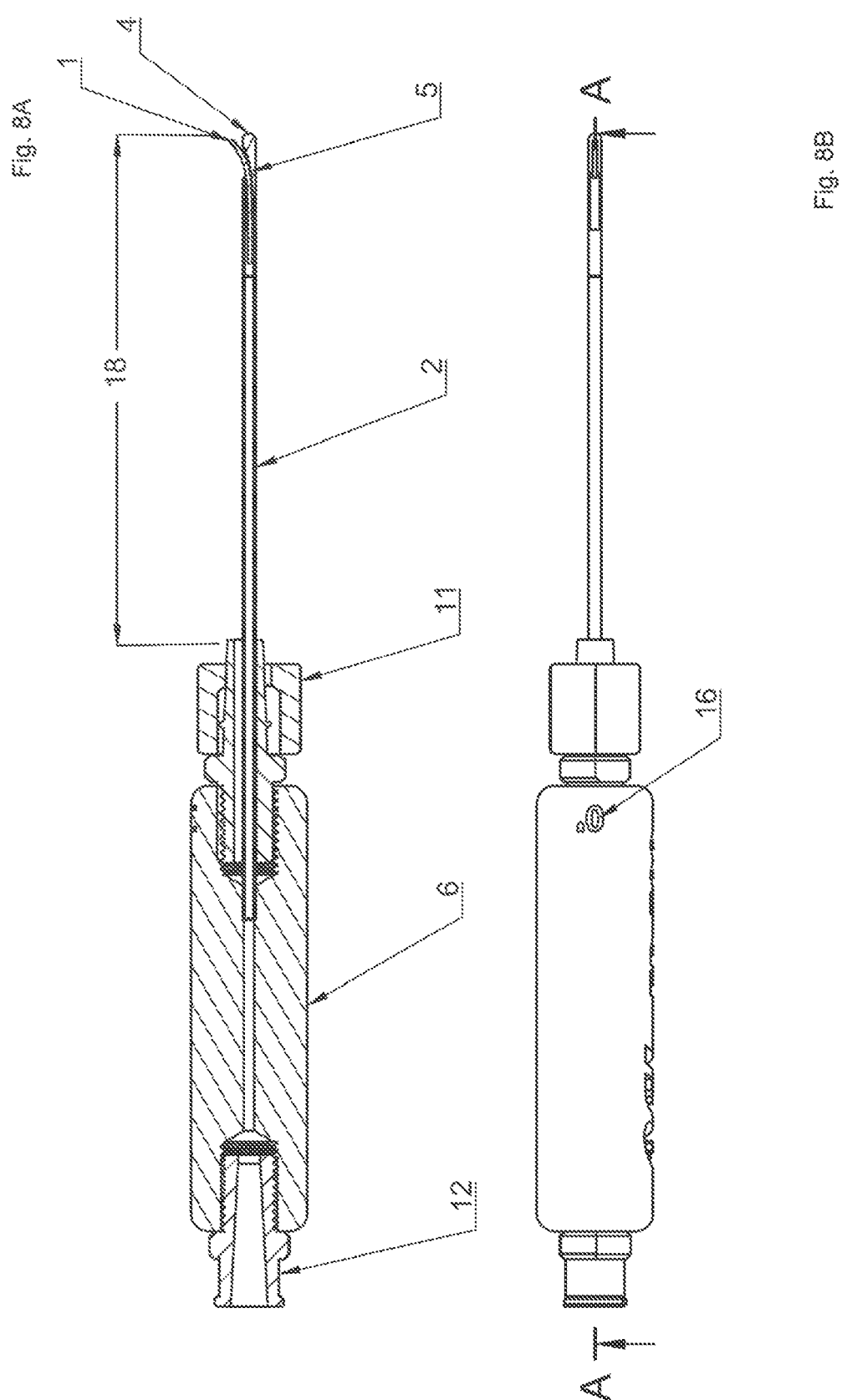
FIG. 8a is a section, side view of the endoscopic system with a cable in an extended position.
FIG. 8b is a top view of the endoscopic system with a cable in an extended position.
Figure 9:
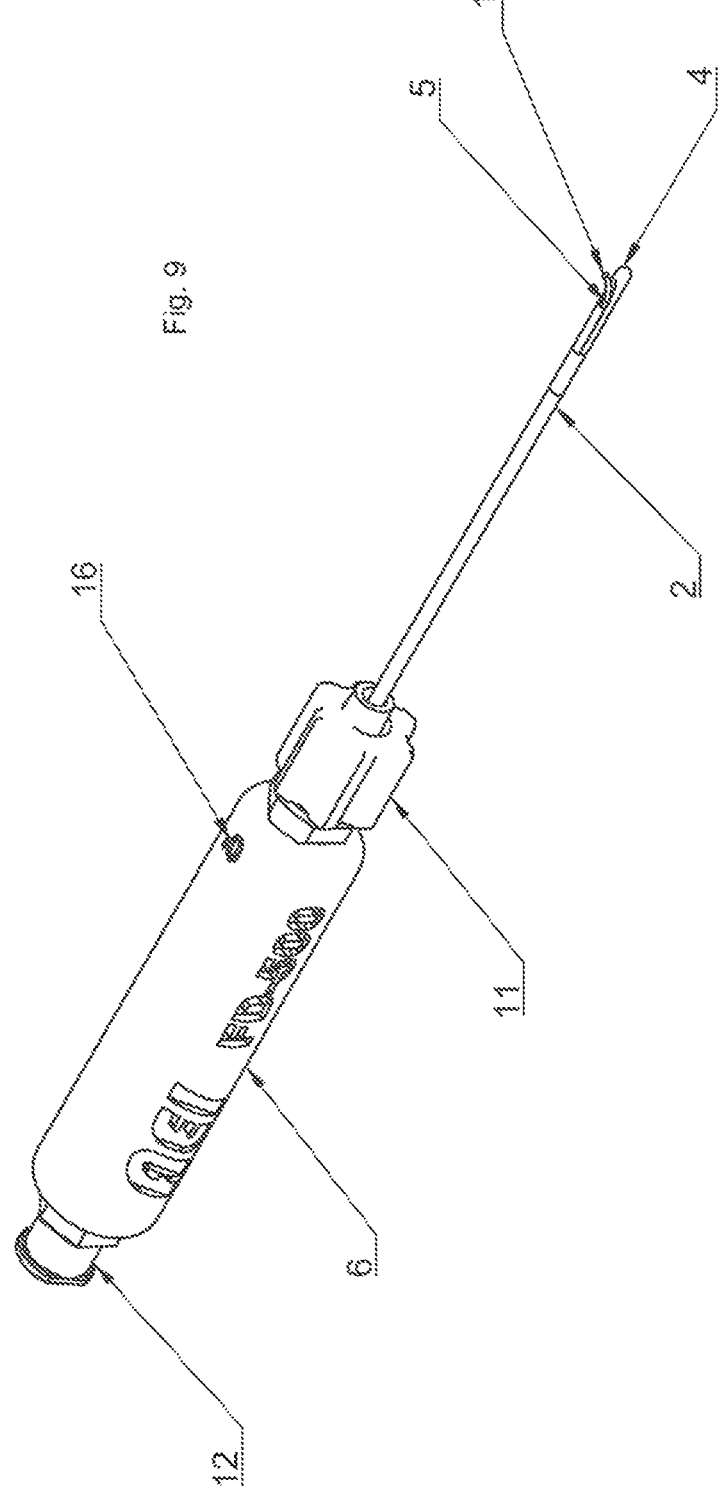
FIG. 9 is an isometric view of the endoscopic system with a cable in an extended position.
Figures 10A, 10B:
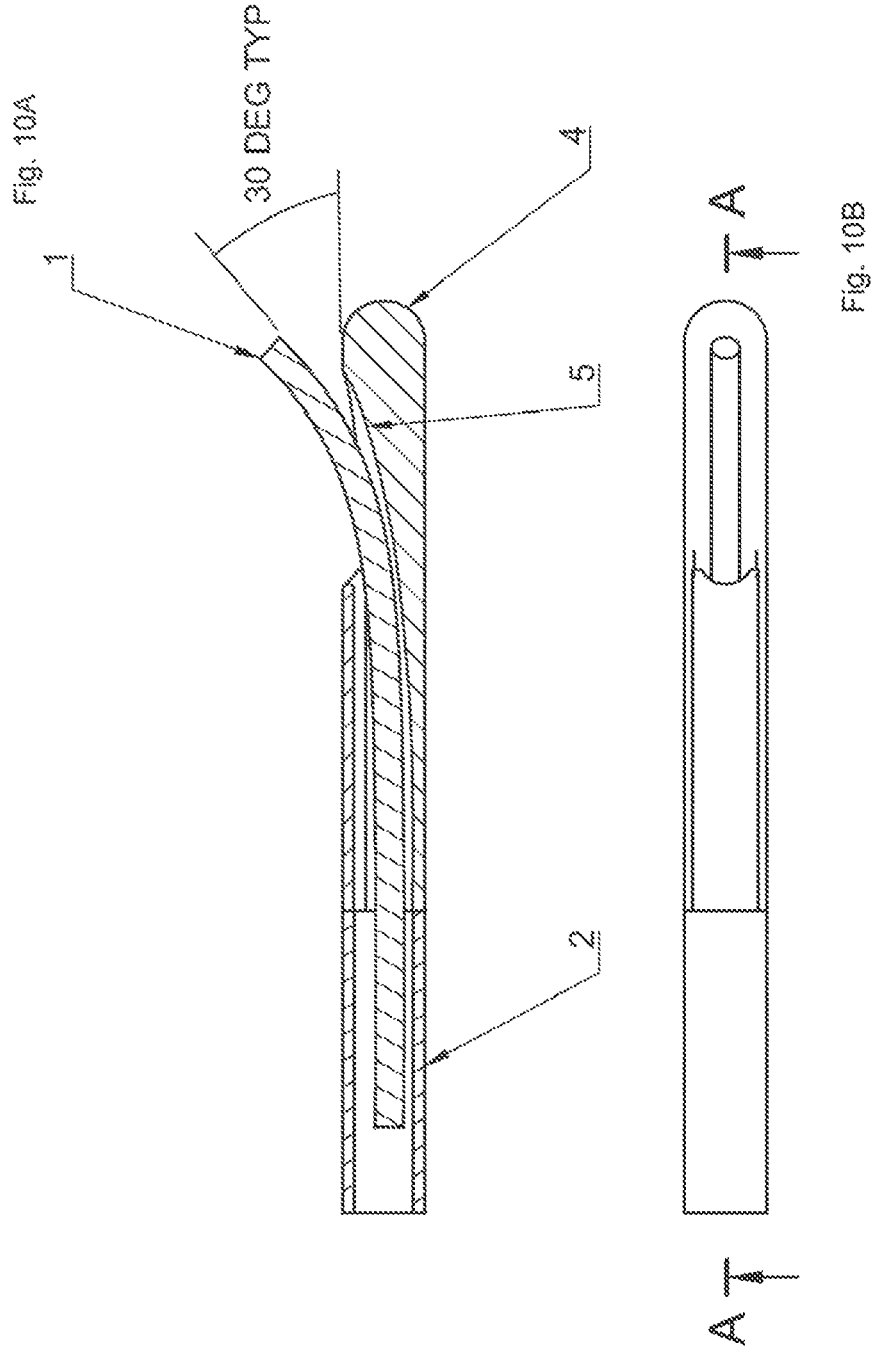
FIG. 10a is a side view of a distal end of the endoscopic system with a cable in an extended position.
FIG. 10b is a top view of the distal end of the endoscopic system with the cable in an extended position.

In FIGS. 8*a*-10*b*, the endoscopic system is shown. In this system, the instrument 1 may be a flexible laser fiber 1 or other devices. The laser fiber 1 and the sheath 2 may be of a fixed length 18. As shown in FIGS. 8*a*-10*b*, not all features shown in FIGS. 1*a*-7 are present, depending on the device being used and the particular safety and control requirements.

Here, the laser fiber 1 is designed specifically to interface with a cannulated endoscope. This interface is controlled by the connection type (in this case a Luer lock fitting 11) and the precise length of the laser fiber and sheath such that, when engaged, the laser fiber's protrusion from the distal end of the endoscope is fixed in length and controllable rotationally. In operation, the device is removed from sterile packaging and the sheath 2 is inserted into the proximal endoscope working channel. It is then passed through the channel until the Luer Lock fittings 11 meet and are engaged. At this point, the device is ready to use.

During the endoscopic procedure, a flexible laser fiber 1 (or another device such as a guide wire, cannula, etc.) is passed through the proximal Luer fitting 12 and exits the distal end at an oblique angle. This angle being adjustable by the design of the elevator 5 at the distal end. The radial position of distal exit may be adjusted by the user via rotation of the proximal control body 6 with visual indicia 16 of said rotational position. The fiber 1 may be retracted within the sheath for repositioning of the endoscope or at the conclusion of the procedure. Depending on the configuration of the distal end of the device, the fiber 1 or other instrument may exit axially (i.e. no elevator 5) or at any oblique angle (such as those between 0 and 90 degrees, inclusive) as provided by numerous elevator designs 5. The oblique angle of exit enabling therapies off the axis of the endoscope, ideally within the center of the field of view, or in radial patterns, all having benefits for specific conditions.

Figure 11:
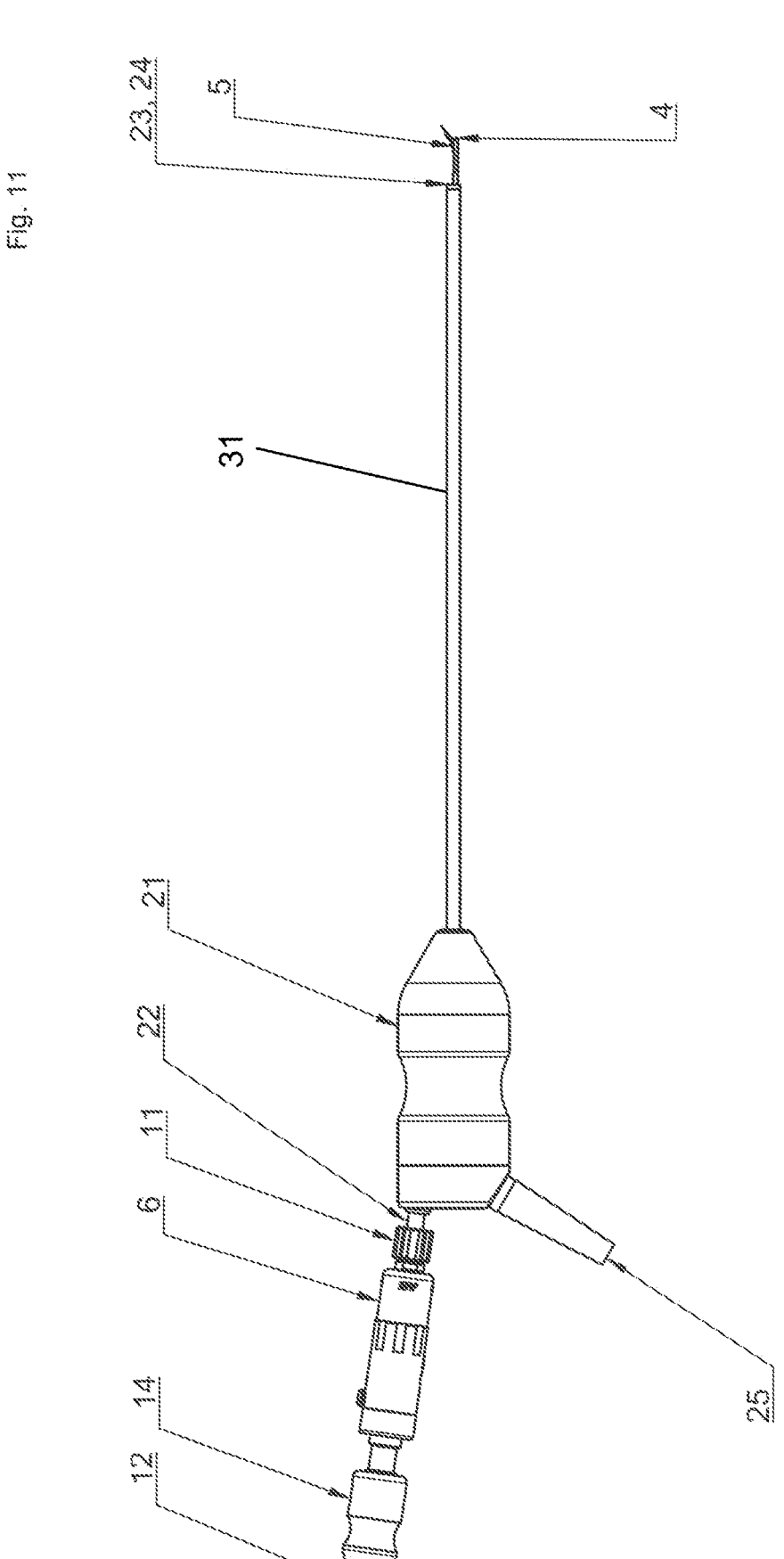
FIG. 11 is a side view of the endoscopic system with an attached endoscope.
Figure 12:
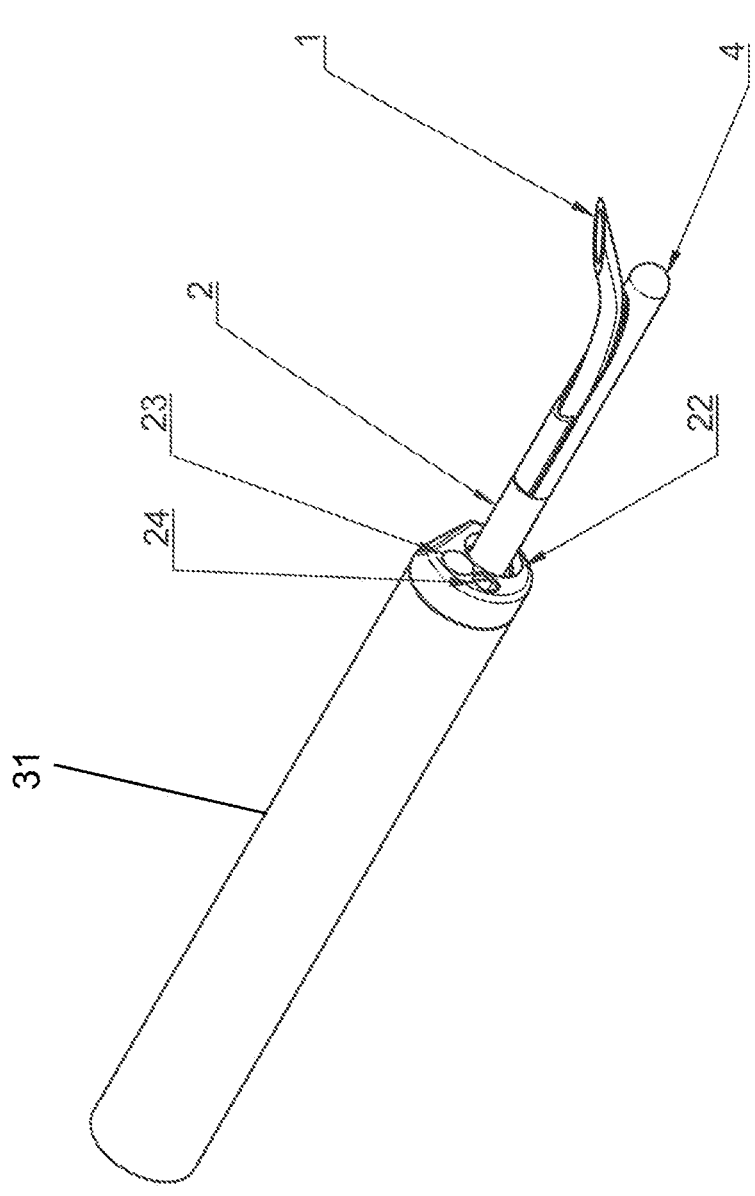
FIG. 12 is an isometric view of a distal end of the endoscopic system with an attached endoscope.
Figures 13A, 13B:
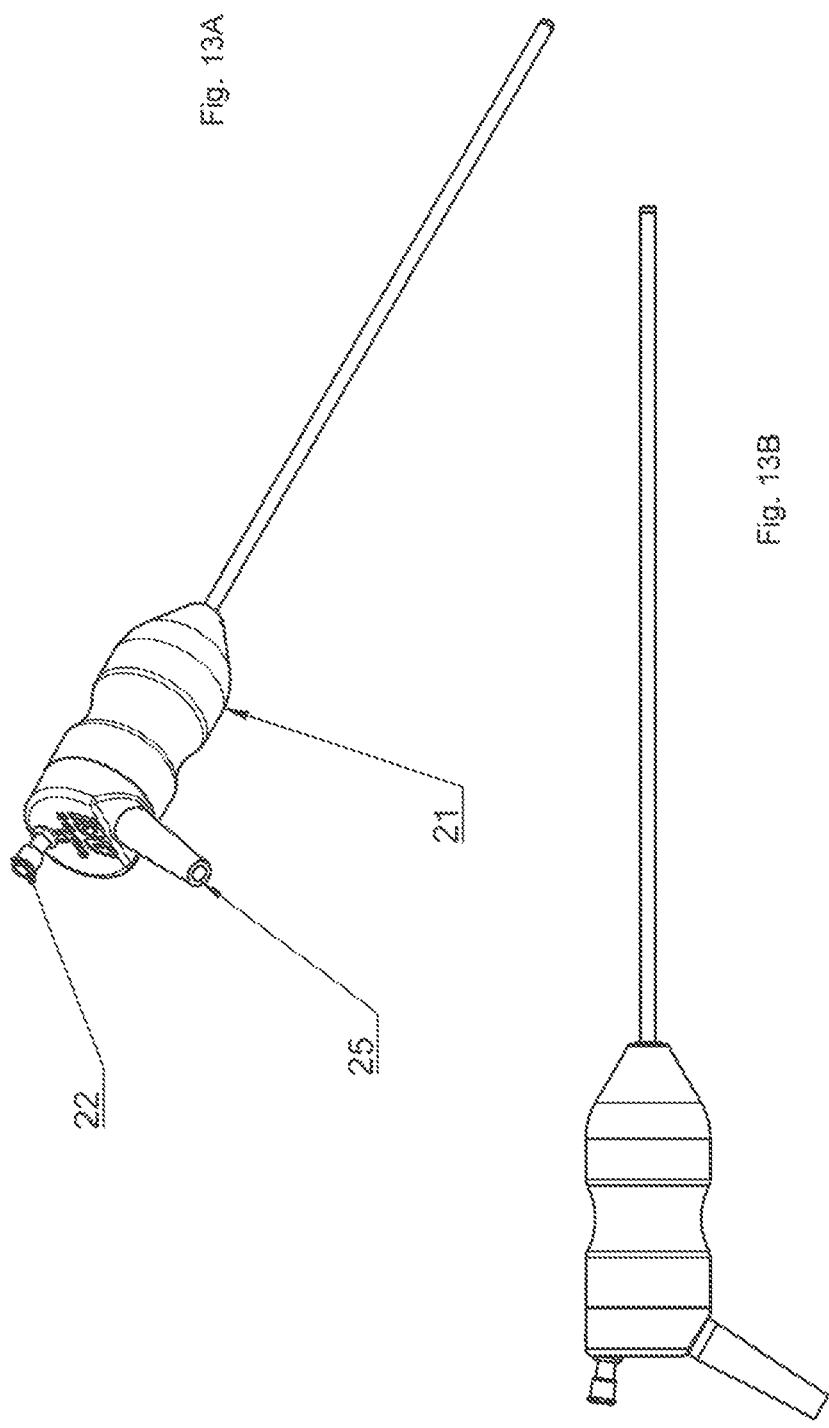
FIG. 13a is an isometric view of the endoscopic system.
FIG. 13b is a side view of the endoscopic system.
Figures 14A, 14B:
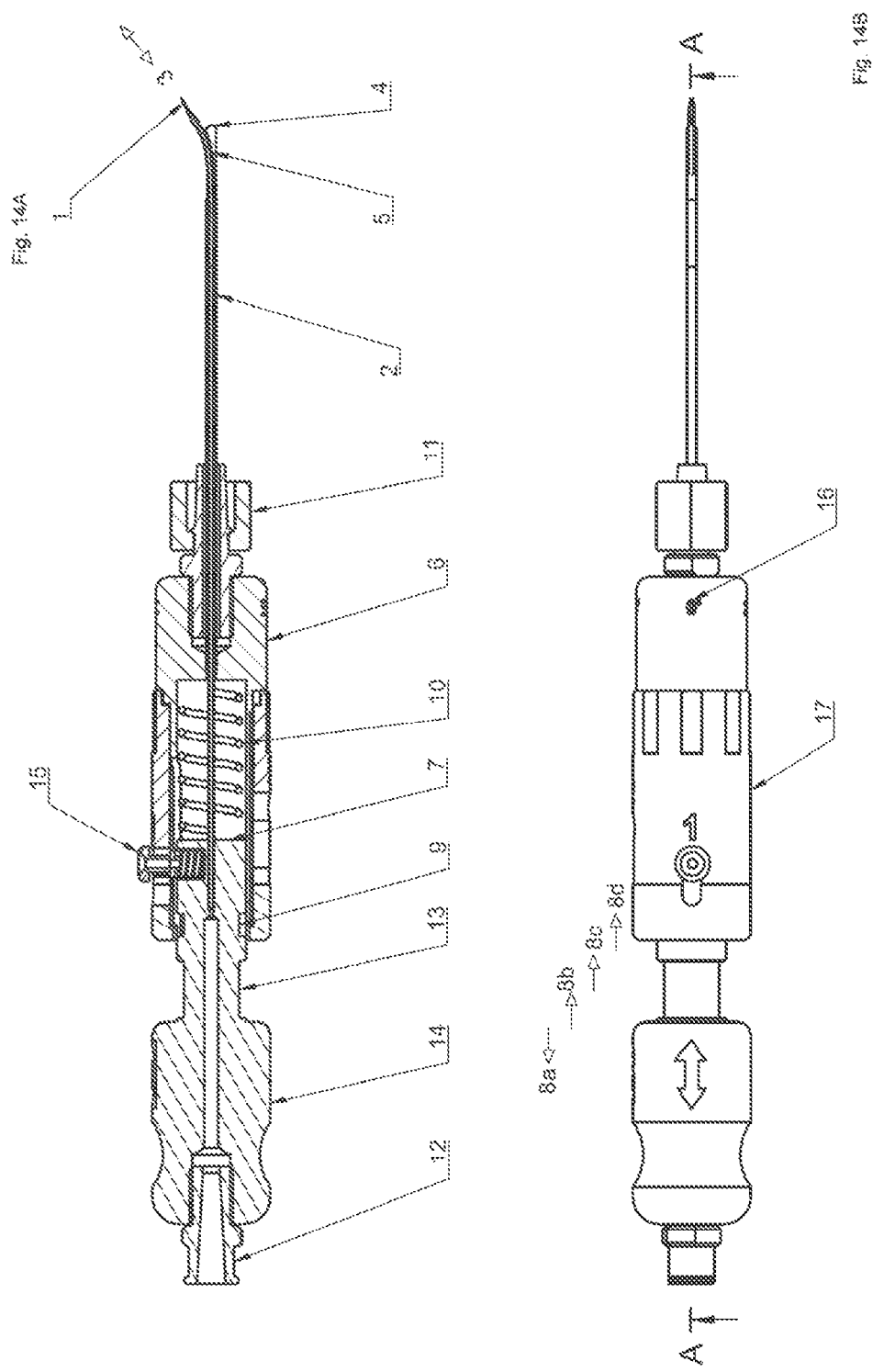
FIG. 14a is a section, side view of the endoscopic system with a needle extended.
FIG. 14b is a top view of the endoscopic system with a needle extended.
Figure 15:
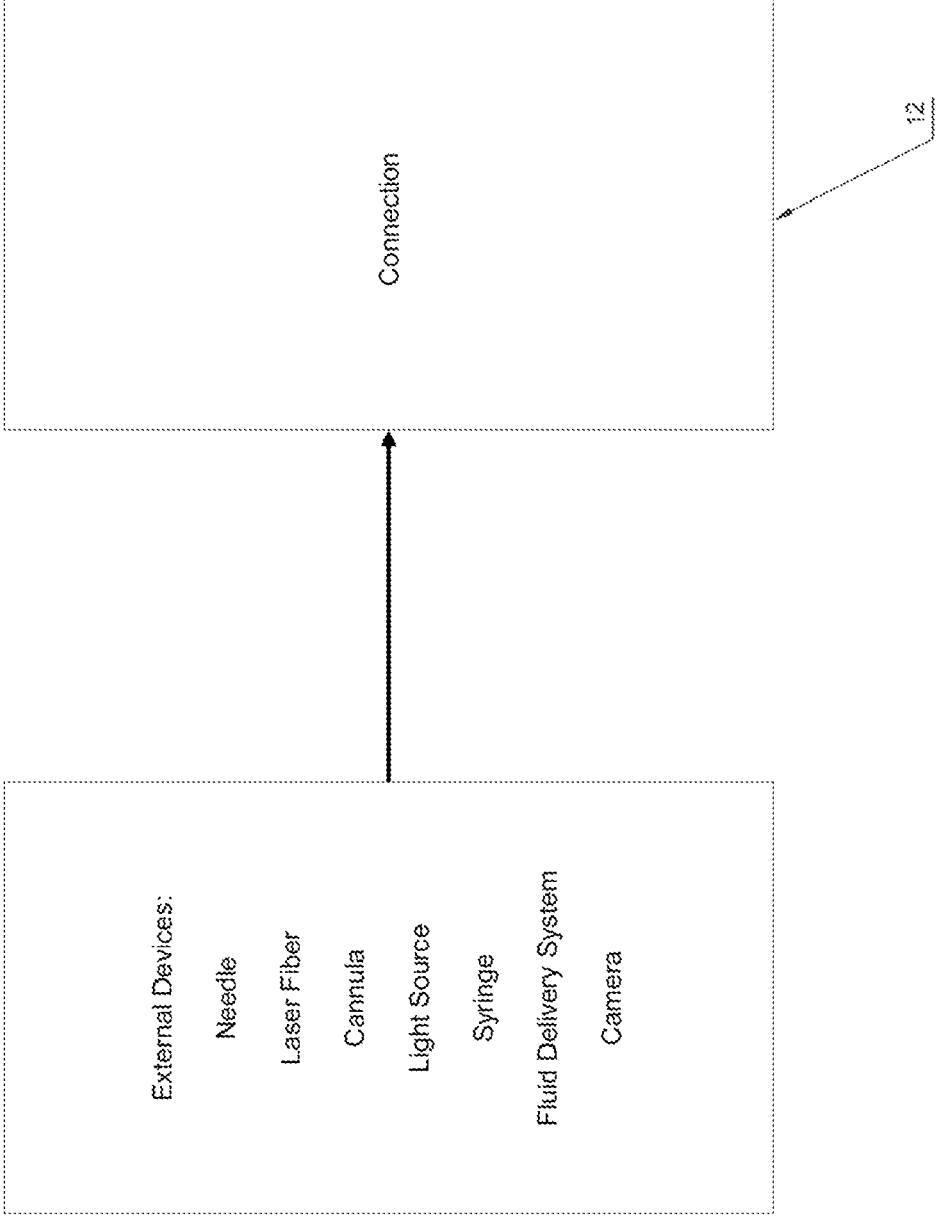
FIG. 15 is a schematic view of exemplary external devices that can connect to the connection.

FIGS. 11-14*b* also show the endoscopic system. The endoscopic system may have an endoscope 21 and a shaft 31, which may be flexible, semi-rigid, or rigid. The endoscope 21 may have one or more working channels 22. The endoscope may have an electronic imaging device 23 and light source 24, such as a CMOS imager, which may be disposed at the distal end. Alternatively, the electronic imaging device 23 may be at the proximal end, with a cable leading to the proximal end where the image is acquired. In either case, the electronic imaging device may have a camera control unit. Power in and signal output may be provided via an umbilical 25 that may be integral or removable.

Instruments 1 are provided to the system that attach directly to the proximal port of the working channel 22 and provide the user certain features and control. For example, as discussed above, proximal knob 14 may control instrument extension and rotation. Luer lock fitting 11 and actuator body 6 may control instrument rotation. Fluid, biologics, and coaxial devices may be introduced through fitting 12. An atraumatic distal end 4 may prevent patient injury and protect the endoscope working channel. In addition, an elevator 5 at the distal end may provide oblique deflection of coaxially passed instrument.

In FIGS. 11-14, an instrument 1 is depicted as a cannula, which provides for fluid or media injection. The cannula and its sheath 2 are proximally attached to the actuator body 6. As discussed above, the axial motion 3 of the cannula can be controlled by a slidably locking piston 7, which may be locked in two or more positions 8a and 8b. A visual indication 9, 13 of the position may be provided, as discussed above. The cannula 1 may be configured to automatically retract via a spring mechanism 10 and a button 15. The actuator body 6 may be connected to the endoscope 21 via a channel fitting 11 (Luer) and may be rotationally adjustable. The connection of the cannula inner diameter to a fluid delivery system may be provided by a connection 12. The connection 12 may also allow for the passage of additional instruments (e.g., a guidewire) to the target organ.

The endoscopic system is designed to address the issues of access to the anatomy and precise control of ancillary instruments for application of numerous therapies. A key to the system is an attachable series of instruments meant to pass through the endoscope working channel. The interface between the endoscope and the instrument is fixed via a Luer Lock or similar connection. The connected instrument has adjustments and mechanics that provide rotation, linear motion, oblique distal exit control, passage of additional fluids and devices, as well as application of energy (Laser, HF, Cryo, etc.). The precise length of the devices may be matched to the endoscope length such that protrusion from the distal end of the endoscope is controlled.

In operation, the endoscopic system is removed from sterile packaging, attached to any ancillary power and control devices, and checked for function. The instrument 1 is removed from sterile packaging checked to assure that it is in "safe" mode (if applicable) and inserted into the proximal endoscope working channel. The instrument shaft is then passed through the working channel until the Luer Lock fittings meet and are engaged. The instrument is then connected to the delivery mechanism for the therapeutic media via a proximal Luer fitting. The endoscopic system is now prepared for use.

In one example, during the endoscopic procedure the instrument 1 may be extended via a proximal knob that employs a "push to lock" linear motion. When in the extended position a red indicator ring 13, for example, will show on the device as a warning. The instrument 1 may be retracted by operating a spring-loaded button mechanism 15 on the control handle 30, said retraction being assisted by an internal compression spring 10 as a safety device. When in the retracted position a green indicator ring 9, for example, will show on the device as an indication of "safe" mode. Multiple extensions and retractions are possible. The instrument 1 is then retracted and confirmed in "safe" mode before withdrawal of the instrument or endoscope from the patient. Multiple types of instruments 1 may be installed and employed during the surgery.

Depending on the configuration of the distal tip, the instrument may exit axially (i.e. no "elevator") or at any oblique angle (such as those between 0 and 90 degrees, inclusive) as provided by numerous elevator designs 5. The oblique angle of exit enabling delivery of therapeutics into lumen walls or organs off the axis of the endoscope, or in radial patterns about the axis of the endoscope, all such actions having benefits for specific conditions. Additionally, the instrument 1 may be used extraluminally, under the direct visualization of the parent endoscope to access vessels or organs enabling the introduction of therapeutics and/or devices.

In compliance with the statute, the present teachings have been described in language more or less specific as to structural and methodical features. It is to be understood, however, that the present teachings are not limited to the specific features shown and described, since the systems and methods herein disclosed comprise preferred forms of putting the present teachings into effect.

For purposes of explanation and not limitation, specific details are set forth such as particular architectures, interfaces, techniques, etc. in order to provide a thorough understanding. In other instances, detailed descriptions of well-known devices, circuits, and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second," etc. for different features/components of the present disclosure are only intended to distinguish the present disclosure from other similar features/components and not to impart any order or hierarchy to the features/components.

To aid the Patent Office and any readers of any patent issued on this application in interpreting the claims appended hereto, Applicant that it does not intend any of the claims or claim elements to invoke 35 U.S.C. 112(f) unless the words "means for" or "step for" are explicitly used in the particular claim.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. An endoscopic system comprising:

a shaft;

a sheath rotatable relative to the shaft and disposed at least partially inside the shaft, the sheath having a distal end with a leading surface and an inner surface;

an instrument provided at least partially inside the sheath and movable relative to the sheath along a longitudinal direction of the sheath; and a handle disposed at a proximal end of the shaft, the handle having a control knob that is slidable to control a longitudinal position of the instrument relative to the sheath, the control knob being (i) rotatable to control a rotational position of the sheath and the inner surface relative to the shaft and (ii) lockable to releasably lock the instrument and sheath in position, wherein the inner surface of the sheath is sloped so as to deflect a distal end of the instrument at a predetermined angle out of the sheath as the distal end of the instrument is longitudinally moved into contact with the inner surface, and wherein the inner surface is configured to, responsive to rotational motion of the sheath by the control knob, be rotated to directionally position the predetermined angle that the distal end of the instrument extends out of the sheath.

2. The endoscopic system of claim 1, wherein the handle includes visual indicators that correspond to the longitudinal position of the instrument.

3. The endoscopic system of claim 1, wherein the control knob is connected to a slidably locking piston that is lockable in a plurality of positions that fix an extended position of the instrument in selectable increments that correspond to the plurality of positions.

4. The endoscopic system of claim 3, wherein the handle includes a spring that contacts a distal end of the slidably locking piston, wherein the spring is configured to, responsive to the slidably locking piston being unlocked, return the slidably locking piston and the instrument to a retracted position.

5. The endoscopic system of claim 4, wherein the handle further comprises a spring-loaded retraction actuator configured to control a retraction of the instrument from one or more extended positions into the retracted position.

6. The endoscopic system of claim 1, wherein the predetermined angle is any angle from zero degrees to 90 degrees.

7. The endoscopic system of claim 1, wherein the instrument is a cannula or a needle, the instrument being configured to permit passage of a second instrument through the instrument.

8. The endoscopic system of claim 1, wherein the instrument is a wire, a laser fiber, a guide wire, a sheath, or other endoscopic tool.

9. The endoscopic system of claim 1, further comprising a light source configured for providing light to the instrument, the instrument being a laser fiber.

10. The endoscopic system of claim 1, the sheath having a proximal end connectable to external devices while permitting straight through passage of the instrument.

11. The endoscopic system of claim 1, the sheath and the instrument being sized such that the instrument extends to a predetermined maximum distance out of the distal end of the sheath.

12. The endoscopic system of claim 1, the sheath being sized such that the sheath and instrument extends a predetermined maximum distance out of the distal end of the shaft.

13. The endoscopic system of claim 1, the sheath having a proximal end connectable to an external device.

14. The endoscopic system of claim 13, wherein the external device is a fluid delivery system.

15. The endoscopic system of claim 1, wherein the instrument is an electrocautery device including a monopolar or bipolar energy device.

16. The endoscopic system of claim 1, wherein the instrument includes an ablative energy source that is a high temperature steam source, a cryotherapy source, a microwave source, a high-frequency ultrasound source, or a laser energy source.

17. The endoscopic system of claim 1, wherein the instrument is an imaging device.

18. An endoscopic system comprising:

a shaft;

an imaging device disposed at a distal end of the shaft;

a light source configured to provide light to the distal end of the shaft;

a sheath disposed at least partially inside the shaft, the sheath having a distal end with a leading surface and an inner surface, the sheath being rotatable relative to the shaft;

an instrument provided at least partially inside the sheath and movable relative to the sheath along a longitudinal direction of the sheath; and a handle disposed at a proximal end of the shaft, the handle having a control knob that is slidable to control a longitudinal position of the instrument relative to the sheath, the control knob being (i) rotatable to control a rotational position of the sheath and the inner surface relative to the shaft and (ii) lockable to releasably lock the instrument and sheath in position;

wherein the inner surface is sloped so as to deflect a distal end of the instrument at a predetermined angle as the distal end of the instrument is longitudinally moved into contact with the inner surface and deflected at the predetermined angle out of the sheath, and wherein the inner surface is configured to, responsive to rotational motion of the sheath by the control knob, be rotated to directionally position the predetermined angle that the distal end of the instrument extends out of the sheath.

19. The endoscopic system of claim 18, wherein the handle includes a slidably locking piston that is lockable in a plurality of positions that fix an extended position of the instrument in selectable increments that correspond to the plurality of positions.

* * * * *